United States Patent [19]

Persico et al.

[11] 4,223,229

[45] Sep. 16, 1980

[54] ORAL RADIATION PROTECTOR APPLIANCE

[76] Inventors: Thomas M. Persico, 1323 Rostraver St.; Richard M. Dudas, 38 Jefferson Dr.; George W. Shusta, 25 Pennsylvania Blvd., all of Monessen, Pa. 15062

[21] Appl. No.: 964,968

[22] Filed: Nov. 30, 1978

[51] Int. Cl.² .................... G21C 11/00; G21F 3/00
[52] U.S. Cl. .................................. 250/515; 250/516
[58] Field of Search ............ 250/515, 479, 516; 2/2, 9

[56] References Cited

U.S. PATENT DOCUMENTS

| | | | |
|---|---|---|---|
| 3,123,831 | 3/1964 | Wells et al. | 250/516 |
| 3,164,840 | 1/1965 | Reynolds et al. | 250/516 |
| 4,024,405 | 5/1977 | Szot | 250/516 |

*Primary Examiner*—Harold A. Dixon
*Attorney, Agent, or Firm*—Sixbey, Friedman & Leedom

[57] ABSTRACT

An oral radiation protector appliance for protecting teeth, gingiva, periodontal bone, salivary glands, and adjacent body areas, against harmful side effects of radiation therapy applied to patient areas such as the head, neck, thyroid etc., which involve substantially large or intense radiation treatments. The protector preferably includes intraoral and extraoral members, the intraoral member serving primarily to protect teeth, gingiva, periodontal bone etc., while the extraoral member covers and shields extraoral anatomy and protects such as the parotid, sublingual and salivary glands.

15 Claims, 5 Drawing Figures

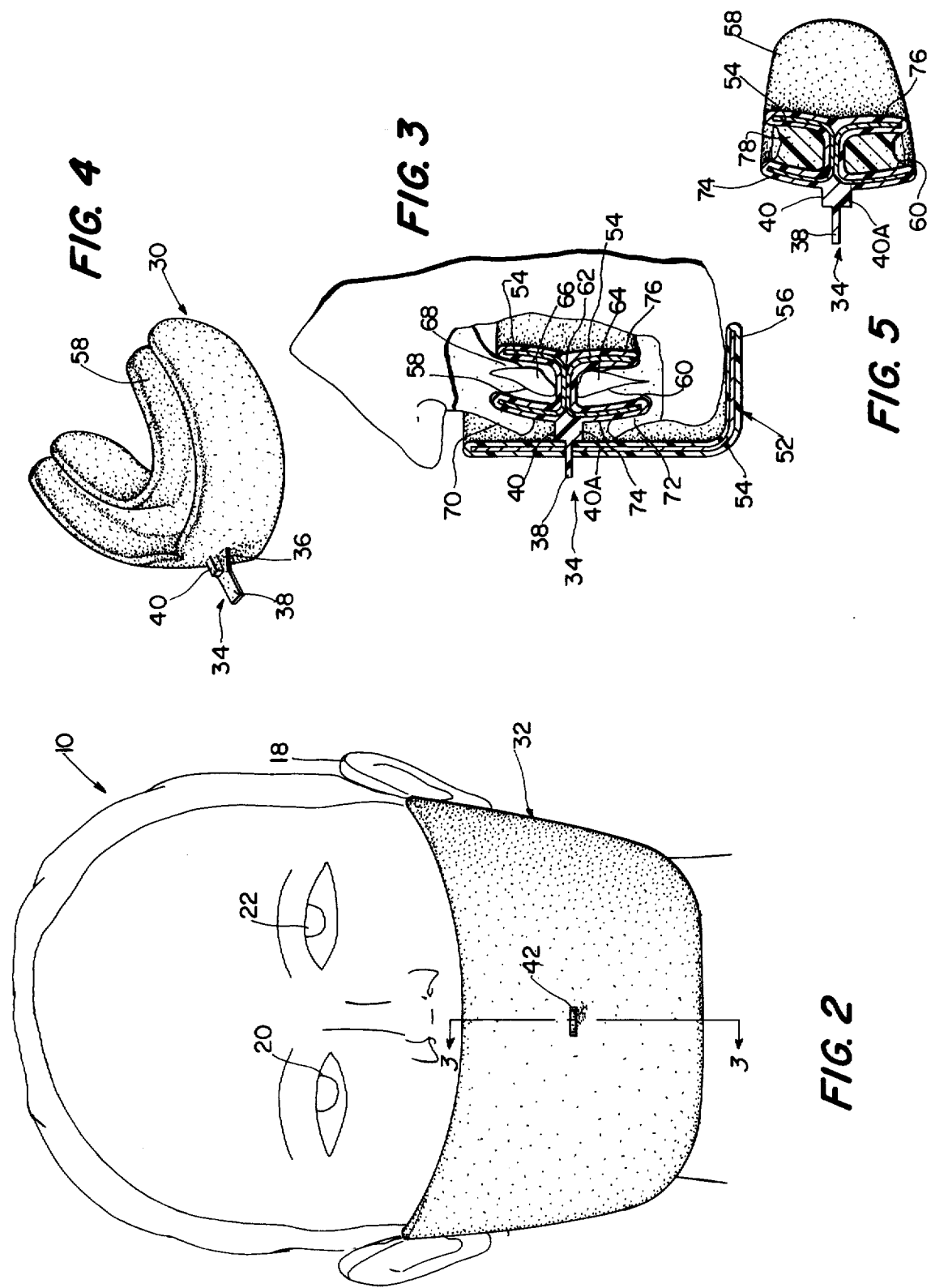

ORAL RADIATION PROTECTOR APPLIANCE

BACKGROUND OF THE INVENTION

The use of X-rays for diagnostic purposes, and radiotherapy, expecially as applicable for treatment of malignancies, has been found necessary and desireable in many phases of dentistry and medicine.

Unnecessary and uncontrolled subjection of the human body, or portions thereof, to radiation, however, including X-rays for diagnostic purposes, or radiation exposure connected with radiotherapy treatment of malignancies, are increasingly recognized as being harmful.

The medical and dental professions accordingly have taken steps attempting to reduce, in so far as possible, the subjection of patients to such harmful radiation, occuring either inadvertently or during intended treatment but perhaps to specifically different parts of the body, or resulting from stray, scattered and surplus rays.

Recent studies have shown, for example, that oral complications occur in patients undergoing radiotherapy treatments for malignancies, even though the malignancies were not in the head and neck. An article in The Journal of the American Dental Association, September 1978, Volume 97, No. 3, pps. 468-472, by Stephen T. Sonis, Andrew L. Sonis and Alan Lieberman, entitled "Oral Complications in Patients Receiving Treatment for Malignancies Other Than of The Head and Neck" discusses the results of a recent study in this connection and reference is made therein to several additional publications & articles reporting the results of other studies. The following ones of the articles are pertinent in regard to the background of the present invention:

Ref. 1. DelRegato, J.A. Dental lesions observed after roentgen therapy in cancer of the buccal cavity, pharynx, and larynx. American Journal of Roentgenology Radium Therapy and Nuclear Medicine, 42:404, Sept. 1939.

Ref. 2 King, E.R., Elzay, R.P. and Dettman, P.M., Effects of ionizing radiation in the human oral cavity and oropharynx, results of a survey. Radiology, 91:990, November 1968.

The use of X-rays for diagnostic purposes in dentistry has also recently been of some concern. Research has generally led the medical and dental professions to avoid unnecessary exposure of patients to X-rays.

It has been found that even very limited amounts of exposure to radiation, especially in children, sometimes causes damage to such glands as the pituitary and thyroid. In efforts to avoid such problems, techniques and apparatus have been developed attempting to either absorb or otherwise shield body areas of a patient from undesired exposure or from stray, or scattered x-rays such as those which normally tend to scatter from the principal stream of X-rays. Preferably the only X-rays allowed to contact human tissue are those necessary in the procedure. Some apparatus of this type is disclosed, for example, in United States Patents Re. 25,773; 3,304,422 and 3,304,423. These patents disclose dental X-ray shields and X-ray aiming means, in conjunction with X-ray film holding devices used in the taking of X-rays of teeth. The stated purpose, and suggested result, is to greatly minimize possible injury to the patient from scattered and surplus X-rays contacting tissues other than those which are intended to be subjected to X-rays.

It is also known to use protective garments or covers, in the nature of aprons and the like, to shield patients and/or certain body areas from stray X-rays during the course of X-ray examination or treatment. An example of an apron type of protective shield is shown in U.S. Pat. No. 3,233,248. Generally, however, such shields and/or protective covers are very heavy and uncomfortable, and varied sizes are required for efficient use with different individual patients.

Another example of a protective shield is shown in U.S. Pat. No. 3,569,713. This patent discloses a shield used in dentistry which is adapted for positionment on, and partially around, the neck of a patient, and is a shield for the thyroid gland of the patient.

There is additionally an increasing awareness in the medical and dental professions of possible serious damages which can be inflicted on teeth, gingiva, dentition, periodontal bone, parotid, sublingual, and salivary glands, and other related near body areas, by harmful side effects of radiation therapy, particularly when the patient receives large radiation doses in the head and neck regions for example.

Research, resulting in part in the above noted articles, which while alluding generally to detrimental and dangerous conditions resulting from negligent use of radiation, fail to completely appreciate the problems, and the techniques and apparatus advanced in the articles, as also in the prior patents, have failed to solve some of the existing problems.

A primary purpose of the present invention is to provide techniques and apparatus which help to overcome some of the existing problems, and to a very substantial extent fulfill a need in the medical and dental professions.

SUMMARY OF THE INVENTION

The present invention is primarily directed to an appliance devised to overcome some of the problems which are resulting effects of radiation, either directly or indirectly applied to teeth and surrounding patient areas and tissues, as also glands, in areas of a patient being treated.

More specifically, the invention teaches a radiation shield intended to protect the teeth, gingiva (gums), periodontal bone and salivary glands against harmful side effects of radiation therapy.

The shield, can consist of or include specifically different materials which are known to protect against radiation, such as lead in sheet form, or lead carried in or by another material, one known material for example consisting of multilayered plastic sheets, an intermediate one of the layers containing fine particles of lead. The shield can vary in thickness and other physical characteristics depending upon the intensity of radiation required for treatments, and also as equated to the patient being treated.

In a preferred form of an appliance for practicing the invention, a composite or combined unit is used including an intraoral portion and an extraoral portion, selectively joinable. The intraoral portion is so designed as to substantially cover the teeth, gingiva, periodontal bone and related tissue to prevent impingement thereon of the radiation rays, and the extraoral portion, which in effect serves as a selectively usable attachment to the intraoral portion, provides a shield which covers the extraoral anatomy of the face and provides protection for the parotid and sublingual and salivary glands.

The conditions among others which the oral radiation protector appliance is intended to protect against include:

1. Salivary gland atrophy and xerostomia (dry mouth). The salivary glands, when exposed to radiation atrophy (shrink) and their function markedly decreases or ceases altogether. This condition lasts from weeks to a permanent loss of function. The patient finds it difficult to chew, swallow and digest food. The food will also adhere to the dentition and periodontal areas increasing the liklihood of caries and periodontal disease.

2. The appliance is also intended to provide protection to the teeth. The dentition is very susceptible to the effects of radiation. Therapeutic radiation in the range of 2500 r to 5000 r causes great injury to teeth and bone. Most organs such as thyroid and brain radiation require over 5000 r. The oral radiation protector appliance will allow a patient to receive large doses in the head and neck region and yet preserve the integrity of the teeth. Should a patient fail to have protection, the dentition becomes susceptible to a condition known as "Radiation Caries." This condition is characterized by demineralization and breaking down of enamel. The teeth become brittle, usually getting cavities in the cervical region, and often breaking off at the gumline.

3. The appliance will also provide protection to children whose teeth are just erupting or are still unerupted. Children often require radiation treatment for head and neck tumors. Hemangioma's in children are also treated by radiation. Radiation therapy, whether direct or indirect, frequently results in stunted undeveloped roots, retarded eruption, and anodontia (missing teeth). The oral radiation protector appliance will aid in preventing this condition.

4. The alveolar bone which holds the teeth has been seen to resorb and become porous as a result of direct and indirect radiation. The teeth loosen and the patient becomes susceptible to periodontitis (pyohorrea).

5. Alveolar bone that has been exposed to radiation has a reduced blood supply and infected teeth are much more severe and dangerous due to this limited blood supply.

6. It has in many instances been the accepted principle to extract the teeth that are in an area to be radiated, as noted in the above mentioned articles. The oral radiation protector appliance in some cases make this procedure unnecessary, since the radiation would not severely damage the teeth and alveolar bone.

7. The oral radiation protector appliance also minimizes a condition known as osteoradionecrosis. The chronic pathosis in this condition is characterized by infection, pain and necrosis. Sequestrae of bone and overlying mucosa are common and in some cases deformity results. This infection can last from months to years, and has also been known to be fatal.

The above listed articles discuss in greater detail some of these problems and it is to be noted that the application of the radiation rays discussed therein is to areas removed from direct impingement on teeth and areas proximate thereto. The direct impingement is understandably more devastating.

BRIEF DESCRIPTION OF THE DRAWINGS

FIG. 2 is a frontal pictorial representation of a human head with intraoral and extraoral shield portions in coacting composite operative positions;

FIG. 3 is a fragmentary view, partly in section, taken on line 3- of FIG. 2; showing in greater detail the composite of the shield portions and their relationship with anatomical areas of a human head;

FIG. 4 is a perspective view of the intraoral shield portion; and

FIG. 5 is a cross-sectional view through an intraoral shield portion and including a core of a foam material therein.

Figure 1:
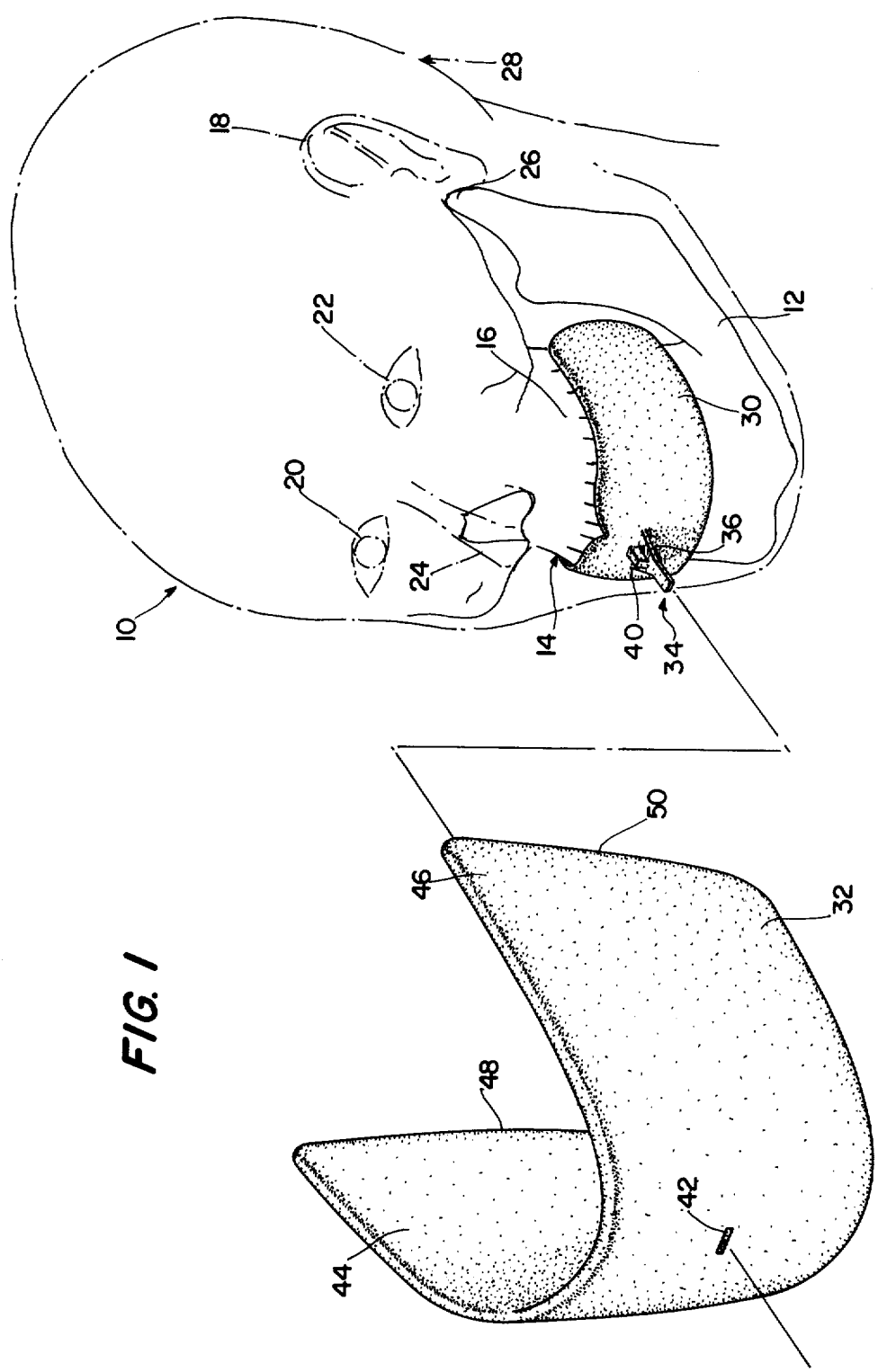
FIG. 1 is an exploded view showing, in a partially skelatonized pictorial representation, a human head with an intraoral shield portion in operative position and the extraoral shield portion in spaced relation.

Referring now in detail to the drawings, a human head is pictorially shown in FIG. 1, and partially skeletonized for better illustration of the present invention. To this end the lower frontal portion of the head has the external face anatomy removed and thus showing as a remainder in relative clarity the lower jaw bone at 12, a portion of the upper jaw at 14, and very broadly there is indicated a section of bone at 16 from which teeth normally arise. The pictorially depicted head additionally shows for physical orientation purposes, an ear 18, eyes at 20 and 22, a nose fragment at 24. The interconnection of upper and lower jaws is broadly indicated at 26. The rear head lobe is broadly indicated at 28.

As pointed out hereinbefore the present invention has as its primary object the protection of teeth, gingiva, periodontal bone, salivary glands and adjacent body areas from direct impingement of uncontrolled rays used, for example, in radiation therapy, and applied to patient areas such as the head neck thyroid etc. This protection is attained, according to the present invention, by means of intraoral and extraoral radiation shield portions. The intraoral shield portion is broadly designated 30 and the extraoral shield portion is broadly indicated at 32. In most circumstances both of the shield portions will be simultaneously used in coacting composite operative positions as shown in FIGS. 2 and 3.

Both the intraoral and extraoral shield portions preferably consist of an inner sheet or layer of lead, covered with a plastic material of a type and having properties to prevent engagement of the lead with any part of the human anatomy. For purposes of assembly into the composite unit when desired, the intra oral shield portion has a forwardly projecting multiple configuration and dimensioned tongue like attachment member 34. A first portion 36 is relatively flat and has a truncated triangular shaped segment narrowed toward the front end, and having a front terminal portion 38 of less width, and of generally rectilinear shape and serving as a frontal extension from the first portion. Superimposed on the first flat truncated portion 36 is a rib 40 which is extended upwardly above the upper surfaces of the first and second frontal portions 36, 38. This rib 40 and a lower rib 40A serve as a positioner, or a stop, for the extraoral shield portion when the two are combined or joined.

The extraoral shield portion 32 has a generally oval shaped opening or hole 42 therethrough. This hole or opening 42 has dimensions such that the attachment member 34 can be inserted therethrough, with the frontal portion 38 extended through the opening, and the rear of the shield will then be engaged against the external surfaces of the portion 36, and restrained from more rearwardly engagement over the member. The ridges or ribs 40, 40A serve as a stop and positioning member at this time.

From FIGS. 1 and 2 it will be seen that the extraoral shield portion 32 is generally curvilinear in shape and adapted to encompass the lower front portion of the head. This extraoral shield includes rearwardly extended slot or wind portions 44 and 46, which in the embodiment shown have an increased depth toward the free rear ends 48 and 50. The dimensions of the extraoral shield is such as to extend over and around the face substantially from ear to ear, and preferably is provided with a lower inwardly directed cap shaped edge 52. The dimensions and configuration provide a shield which covers the extraoral anatomy of the face, and provides protection for the parotid, sublingual and salivary glands. Under some circumstances use of the extraoral portion may not be desirable, such as when X-rays of the glands, for example, are to be taken. Otherwise the extraoral shield portion would normally be combined with the intraoral shield portion mounting on the attachment 34. The area of covering protection can be seen and more readily understood from FIGS. 2 and 3 of the drawings. This extraoral shield portion, similar to the intraoral shield portion, is constructed with an inner lead sheet or layer member 54, and a plastic material cover or coating 56 of a suitable material. The primary function of this plastic coating is to prevent contact between the lead and any part of the anatomy. Representative of such materials are synthetic resins like methyl methacrylates, synthetic polyamides such as nylon, and Dow Corning silicones for biological use.

The intraoral shield portion indicated broadly at 30 in FIG. 1 is shown in greater detail in FIGS. 3 and 4. This member is somewhat in the nature or configuration of dental impression trays, known in the dental profession, and for practical usage may, for example, be provided in three different adult sizes and one or more children sizes. These members have generally curvilinear configurations commensurate with the normal dentition of humans, and include an upper cup shaped section 58 and an inverted lower cup shaped section 60 which are joined or interconnected at their apices 62. The configurations and dimensions of these cup shaped sections are devised to provide maximum possible coverage of lower teeth 64, upper teeth 66 and related gingiva or gum areas 68, the dimensions being of course controlled by the depths defined between upper lip 70 and lower lip 72 and the related gum and tooth regions. This relationship is clearly shown in FIG. 3 with the front cup surfaces 74 being interposed between the teeth and inner surfaces of the lips and a rear cup surface 76 being positioned behind the teeth in the mouth. The plastic material can have physical characteristics such that the teeth can bite on the flat center bases or bottoms of the cup shaped sections to hold it in place, or alternatively, as shown in FIG. 5, the cups can be filled with a soft and resilient material 78 such as a polyfoam for example. This material is not necessary however.

The thickness of the lead sheet can of course vary, although roughly the dimension will be between one millimeter and 5 millimeters. This will depend to some extent on the intensity of radiation used.

Under normal circumstances the intraoral shield portion is designed for a single usage, that is, not to be cleansed and/or sterilized and then used with a different patient. The extraoral shield portion is reusable however, since it is not normally necessary to sterilize this unit.

It is obvious that the specific composition and/or materials used for the shield portions can vary as known in the art.

The attachment 34 not only serves in the nature of an interlocking key between the two portions, but additionally can serve as a handle for manipulation of the device.

While a preferred embodiment of the invention has been shown and described, manifestly minor changes can be effected without departing from the scope and spirit of the invention as defined in, and limited solely by, the appended claims.

We claim:

1. An oral radiation protector appliance for protecting human anatomy against harmful side effects of radiation therapy comprising an intraoral portion and an extraoral portion, said portions being formed of material substantially impervious to penetration therethrough of radiation rays, said intraoral portion substantially covering and protecting the frontal, upper and rear surfaces of the teeth, the gingiva and periodontal bone, the extraoral portion covering extraoral areas of the face and protecting the parotid and sublingual and salivary glands.

2. An oral radiation protector as claimed in claim 1, said intraoral portion being substantially U-shaped to encompass the teeth and adjacent anatomy areas of a patient.

3. An oral radiation protector as claimed in claim 1, said intraoral portion including substantially U-shaped upper and lower sections joined in back to back relationship to encompass the upper and lower teeth and adjacent anatomy areas of a patient.

4. An oral radiation protector as claimed in claim 1, said material in said intraoral portion including a layer of radiation shielding material and a covering of a plastic material.

5. An oral radiation protector as claimed in claim 1, said material in said intraoral portion including a lead sheet and a coating of a plastic material thereover.

6. An oral radiation protector as claimed in claims 1 or 5, said material of said extraoral portion including a lead sheet.

7. An oral radiation protector as claimed in claims 1, 2 or 3, wherein said intraoral portion includes a projection thereon extending forwardly and external of the mouth of a patient, said extraoral portion having an opening therethrough for detachable mounting attachment of said extraoral portion on said projection.

8. An oral radiation protector appliance for protecting teeth, gingiva, periodontal or alveola bone, salivary glands, and adjacent body areas, of a patient against harmful radiation therapy side effects comprising an intraoral member and an extraoral member, said extraoral member being selectively attachable to and detachable from said intraoral member for selected combined appliance usage, or for separate use of said intraoral member, said intraoral member substantially covering the teeth, gingiva, periodontal or alveolar bone, and said extraoral member substantially covering extraoral anatomy of the face to protect the parotid and sublingual and salivary glands.

9. An appliance as claimed in claim 8, said intraoral and said extraoral members respectively having coacting means for joining said members externally of a patients mouth.

10. An appliance as claimed in claim 9, said coacting means comprising a projection on said intraoral member adapted for extension externally of a patient's mouth and an opening through said extraoral member into which said projection is insertable to thereby mount and attach said extraoral member on said intraoral member.

11. A radiation protective shield for preventing direct impingement of radiation rays on teeth, dentine, alveolar bone, and adjacent body tissues of a person being subjected to radiation therapy, comprising an intraoral shield portion and an extraoral shield portion, said intraoral portion including at least in part a radiation shielding material, having a shape conforming to the curvilinear configuration of a human dentition and adapted for disposition within the mouth of the person, and with at least a front portion thereof interposed between the inner sides of the mouth lip portions and forward sides of the teeth and associated gingiva and alveolar bone, the intraoral shield having a depth serving to substantially cover the upper and lower sets of dentitions and tissues and bone associated with the teeth, said extraoral shield, consisting of a curvilinear shaped sheet of radiation shielding material and being selectively attachable to and supportable by said intraoral shield and disposed thereby externally of the mouth of the person, said extraoral portion being of shape and size to cover a substantial area of the extraoral anatomy of the face of the person to thereby intercept rays and prevent direct and/or stray impingement thereon.

12. A radiation protective shield as claimed in claim 11, said intraoral shield including upper and lower channel shaped members adapted to substantially contain within the physical dimensions thereof the upper and lower gingival, teeth, aleveolar bone and adjacent areas of a user person, the channel shaped members being medially connected and opening respectively upwardly and downwardly, and thereby engageable over and encompassing the upper and lower teeth sets.

13. A radiation protective shield as claimed in claim 12, said intraoral shield having a frontal projection thereon adapted for external projection from the persons mouth, said extraoral shield having an opening therein engageable with said projection and constituting a support for said extraoral shield.

14. A radiation protective shield as claimed in claim 13, said material including a lead sheet, said intraoral shield being coated with a plastic material to prevent tooth and internal mouth contact with the lead material.

15. A radiation protective shield as claimed in claim 14, the plastic material coating on said intraoral shield being of soft and resilient texture but of a strength to normally prevent penetration by the teeth of the person.

* * * * *